United States Patent
Miyata et al.

(10) Patent No.: US 9,895,732 B2
(45) Date of Patent: Feb. 20, 2018

(54) MAGNESIUM BASE ALLOY TUBE AND ITS MANUFACTURING METHOD

(71) Applicant: GOHSYU CORPORATION, Shiga (JP)

(72) Inventors: Toshinobu Miyata, Shiga (JP); Kenji Tasaki, Shiga (JP); Yoshinori Goho, Shiga (JP)

(73) Assignee: GOHSYU CORPORATION, Shiga (JP)

( * ) Notice: Subject to any disclaimer, the term of this patent is extended or adjusted under 35 U.S.C. 154(b) by 205 days.

(21) Appl. No.: 14/887,405

(22) Filed: Oct. 20, 2015

(65) Prior Publication Data

US 2017/0014881 A1 Jan. 19, 2017

(30) Foreign Application Priority Data

Jul. 15, 2015 (JP) ................................. 2015-141461

(51) Int. Cl.

| | | |
|---|---|---|
| *B21C 23/00* | (2006.01) | |
| *A61F 2/82* | (2013.01) | |
| *B22F 5/10* | (2006.01) | |
| *C22C 23/02* | (2006.01) | |
| *B21C 23/10* | (2006.01) | |
| *B21C 29/04* | (2006.01) | |
| *B21C 33/00* | (2006.01) | |
| *B22F 3/20* | (2006.01) | |

(52) U.S. Cl.
CPC .............. *B21C 23/002* (2013.01); *A61F 2/82* (2013.01); *B21C 23/004* (2013.01); *B21C 23/10* (2013.01); *B21C 29/04* (2013.01); *B21C 33/00* (2013.01); *B22F 5/106* (2013.01); *C22C 23/02* (2013.01); *A61F 2310/00041* (2013.01); *B22F 3/20* (2013.01); *B22F 2003/208* (2013.01); *B22F 2202/01* (2013.01); *B22F 2998/10* (2013.01); *B22F 2999/00* (2013.01)

(58) Field of Classification Search
CPC .............................. B21C 23/002; A61F 23/002
USPC ........................................................ 428/586
See application file for complete search history.

(56) References Cited

FOREIGN PATENT DOCUMENTS

| | | | |
|---|---|---|---|
| CA | 2464442 | * 9/2003 | ............. C22C 23/00 |
| JP | 3597186 | 12/2004 | |
| JP | 2014-21454 | 2/2014 | |
| WO | 2014/021454 | 2/2014 | |

OTHER PUBLICATIONS

CA 2464442; Abstract; Magnesium Base Alloy Tube and Method for Manufacture Thereof Sep. 12, 2003.*

* cited by examiner

*Primary Examiner* — Terressa Boykin
(74) *Attorney, Agent, or Firm* — Wenderoth, Lind & Ponack, L.L.P.

(57) ABSTRACT

A raw material of aluminum base alloy is extruded and formed by using a forming pattern comprising an upper pattern having plural through-holes for supplying the raw material into diaphragms of equal angles on the circumference and circular cylindrical protrusions positioned in the center of plural through-holes so as to be surrounded by plural through-holes at the exit side of the through-holes, and a lower pattern positioned in the concave portions commonly penetrating at the exit of the plural through-holes of the upper pattern, having through-holes for inserting the protrusions of circular circumference of the upper pattern by providing a tube forming gap, positioned in the center of concave portions of the concave portions in the circular columnar shape of the upper pattern.

4 Claims, 10 Drawing Sheets

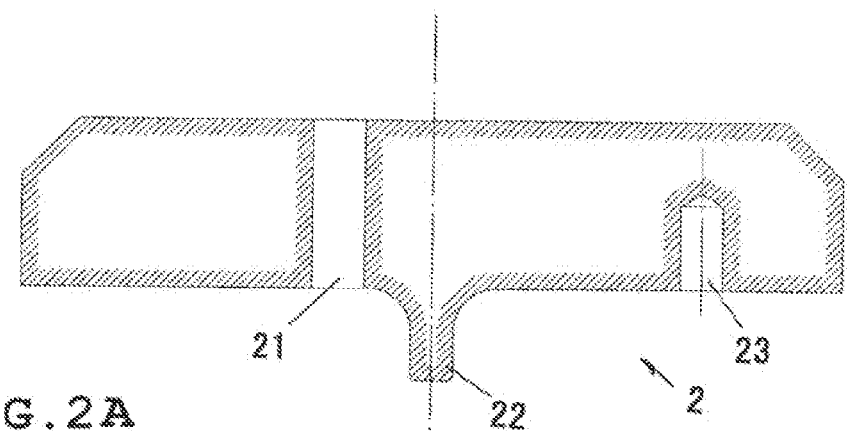
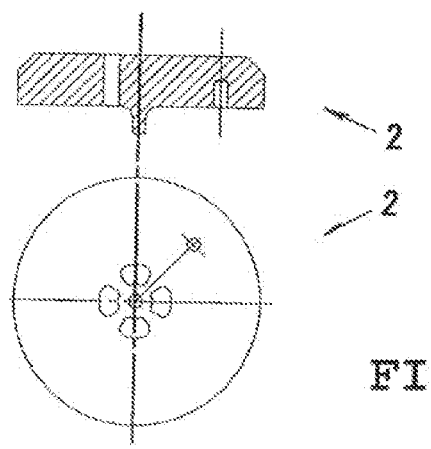
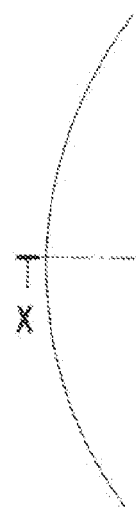
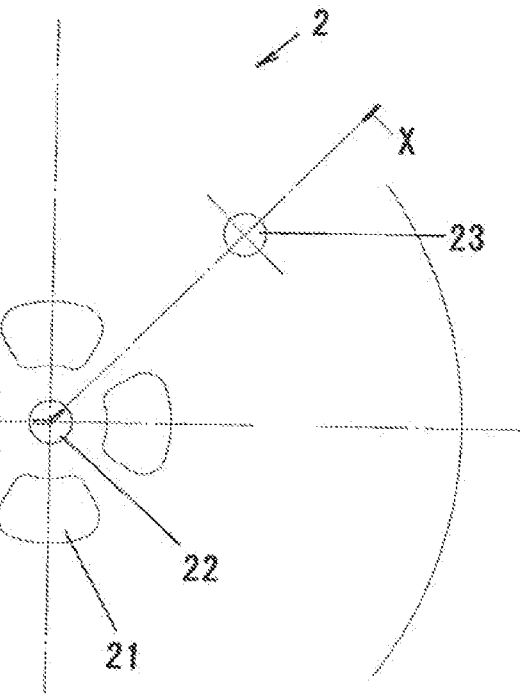
FIG.2B
FIG.2A
FIG.2C
FIG.2D

FIG. 3B
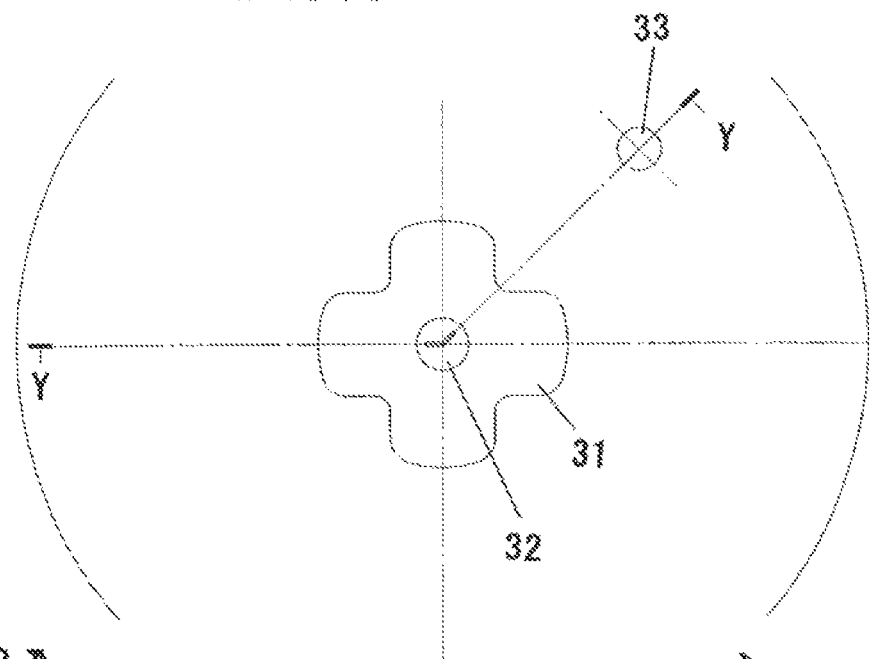
FIG. 3A
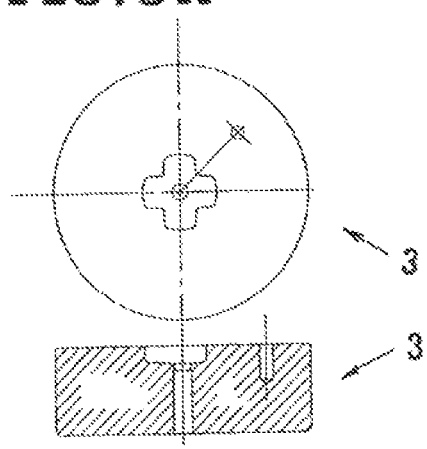
FIG. 3C
FIG. 3D
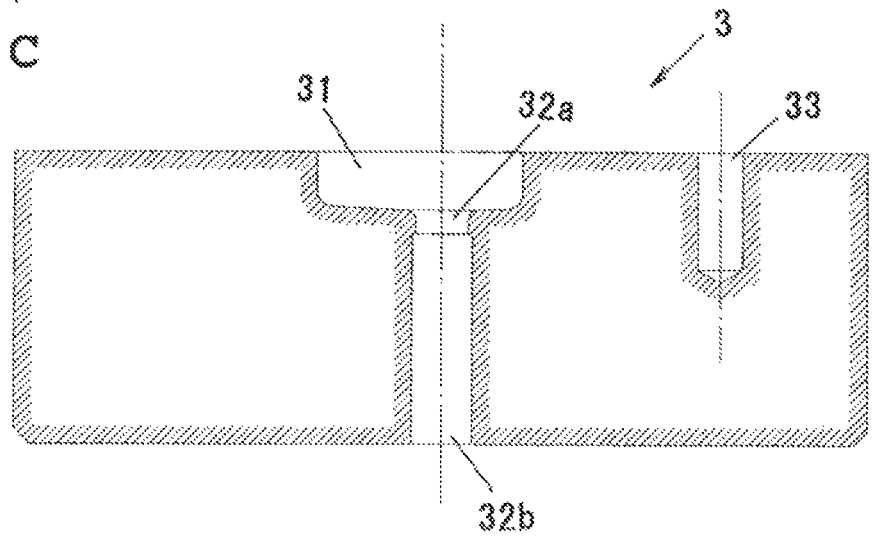

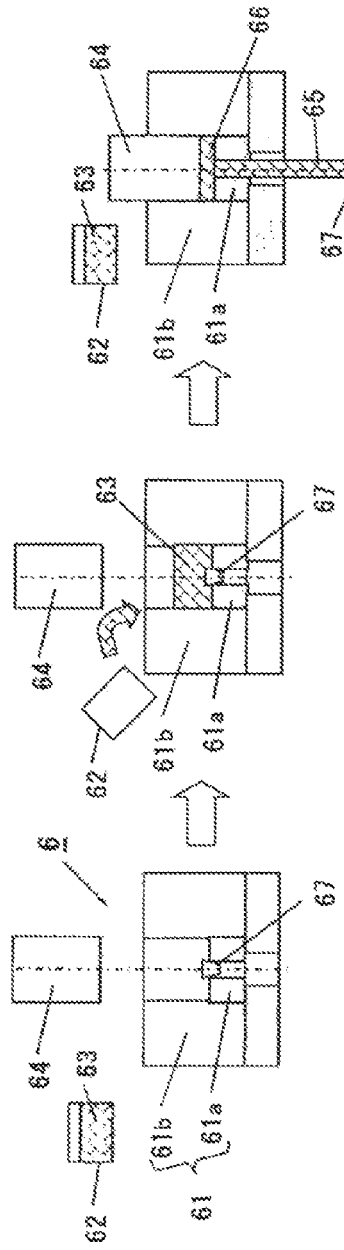

US 9,895,732 B2

MAGNESIUM BASE ALLOY TUBE AND ITS MANUFACTURING METHOD

TECHNICAL FIELD

The present invention relates to a magnesium base alloy tube and its manufacturing method, and more particularly to a small-diameter magnesium base alloy tube and its manufacturing method preferably usable in manufacture of a stent (as an effective therapeutic method of coronary arterial diseases such as angina or myocardial infarction, a percutaneous coronary intervention (PCI) is known, and herein it refers to a reticular metal tube of thin-wall fine tube manufactured by laser processing or the like for use in coronary arterial disease in this PCI.

BACKGROUND ART

Magnesium comprises ¼ of iron and ⅔ of aluminum by specific gravity, and it noted as a metal having the smallest specific gravity as structural metals. In particular, magnesium base alloy has a higher rigidity than other metals, and is easier to lower in weight, and is developed in various applications as structural materials in various industrial fields (see, for example, patent document 1).

At the same time, owing to its excellent biocompatible properties, magnesium base alloy is being intensively developed in various industrial applications as medical materials, for instance, stent (see, for example, patent document 2)

However, magnesium base alloy is small in slip coefficient number at ordinary temperature, and is low in cold processability, and is hence actually limited in applications in a wide range, and in particular in the case of manufacture of a small-diameter magnesium base alloy tube used in manufacture of a stent, because of low processability, in order to obtain a large sectional area reduction rate, it is necessary to manufacture by way of a special manufacturing process, for example, by passing through multiple dice having tubular materials arranged in a row, and in addition to an extra cost required for manufacture, it is more likely to have affects of processing and hardening[[g, and it was hence difficult to obtain a small-diameter magnesium base alloy tube long in length, high in dimensional precision, and excellent in mechanical properties used for manufacture of a stent.

PRIOR TECHNICAL PAPERS

Patent Document

[Patent document 1] Japanese Patent Document Publication No. 3597186
[Patent document 2] International Patent Document Publication No. 2014/021454

OUTLINE OF THE INVENTION

Problems to be Solved by the Invention

The present invention relates to the conventional magnesium base alloy product, more particularly to a problem of a small-diameter magnesium base alloy, and it is a primary object thereof to present a small-diameter magnesium base alloy tube and its manufacturing method long in length, high in dimensional precision, and excellent in mechanical properties.

Means for Solving the Problems

To achieve the above objet, the magnesium base alloy tube of the invention is characterized by the outside diameter of 1.0 to 6.0 mm, the inside diameter of 0.8 to 5.5 mm, the overall length of 500 mm or more, the coaxiality of 20 μm or less, and the elongation of 10% or more.

The manufacturing method of the magnesium base alloy tube of the invention is a method of manufacturing the magnesium base alloy tube, being characterized by extruding and forming a raw material of magnesium base alloy, by using an extrusion-forming die comprising an upper pattern having circular cylindrical protrusions of a plate shape positioned in the center of plural through-holes so as to be surrounded by plural through-holes for supplying the raw material into diaphragms of equal angles on the circumference, and a lower pattern positioned in the concave portions commonly penetrating at the exit of the plural through-holes of the upper pattern, having through-holes for inserting the protrusions of circular circumference of the upper pattern by providing wind-shaped gap, positioned in the center of concave portions of the concave portions in the circular columnar shape of the upper pattern In this case, as the raw material of the magnesium base alloy, any powder, cast material or extrusion forming material may be used.

Effects of the Invention

According to the magnesium base alloy tube and its manufacturing method of the invention, it is possible to present a small-diameter magnesium base alloy tube suited to manufacture of a stent, long in length, high in dimensional precision, and excellent in mechanical properties, and its manufacturing method.

BRIEF DESCRIPTION OF THE DRAWINGS

FIGS. 2A-2D show an upper pattern of a forming pattern of the manufacturing apparatus, wherein: FIG. 2A is an x-x sectional view of a sectional view FIG. 2D, FIG. 2C is a bottom view, FIG. 2B is a magnified view of FIG. 2A, and FIG. 2D is a magnified view of FIG. 2C.

FIGS. 3A-3D show a lower pattern of a forming pattern of the manufacturing apparatus, wherein: FIG. 3A is a plan view, FIG. 3C is a sectional view (a Y-Y sectional view of FIG. 3B, FIG. 3B is a magnified view of FIG. 3A, and FIG. 3D is a magnified view of FIG. 3C.

FIGS. 10A-10E are explanatory diagrams showing an example of a manufacturing process of a magnesium base alloy tube to be used as a raw material in a manufacturing method of a magnesium base alloy tube of the invention.

BEST MODE FOR CARRYING OUT THE INVENTION

Figure 1:
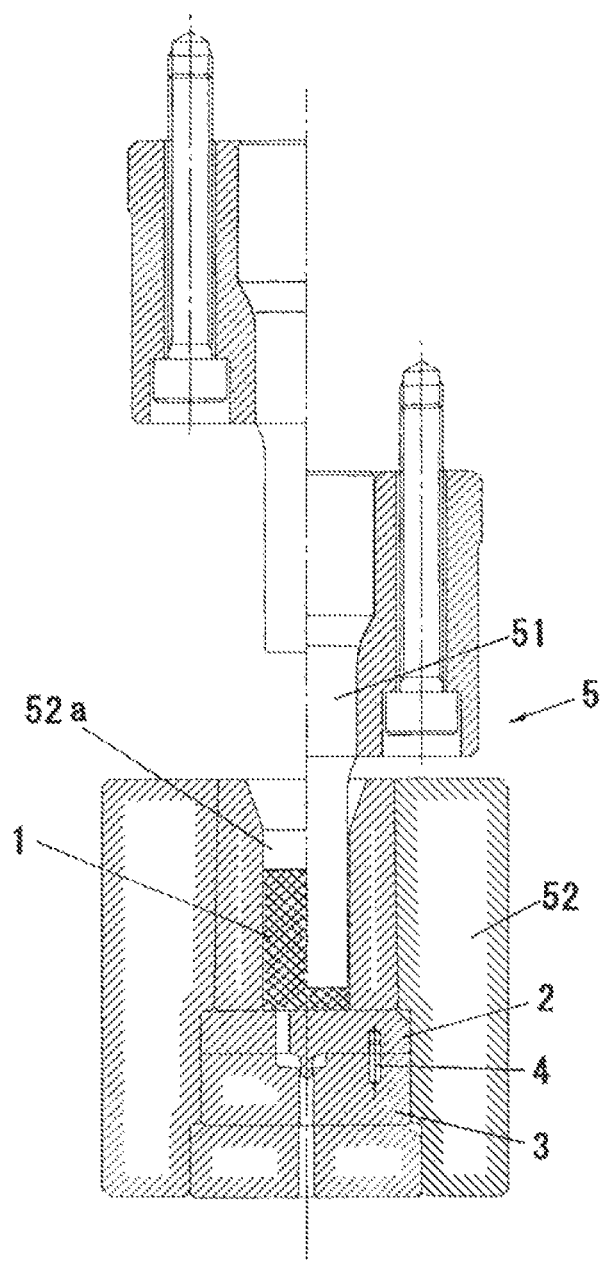
FIG. 1 is an explanatory diagram hosing an example of a manufacturing apparatus for executing a manufacturing apparatus of a magnesium base alloy tube of the invention.

Hereinafter, the magnesium base alloy tube and its manufacturing method of the invention are specifically described while referring to embodiments and the accompanying drawings.

FIG. 1 to FIG. 3D show examples of the manufacturing apparatus for executing the manufacturing method of the magnesium base alloy tube.

This manufacturing apparatus is a forming pattern, which comprises an upper pattern 2 having plural (four in this example) penetration holes 21 for supplying a raw material 1 of a magnesium base alloy to equal angle intervals on the circumference and circular columnar protrusions 22 positioned in the center of the plural penetration holes 21 so as to be surrounded by the penetration holes 21 at the outlet side of the penetration holes 21, and a lower pattern 3 having concave parts 31 of a specific shape (cross shape in this example) commonly penetrating the outlet of the plural penetration holes 21 of the upper pattern 2 and penetration holes 32 positioned in the center of this concave part 31, in which the protrusions 22 of the circular columnar shape of the upper pattern 2 are to be inserted, is installed in a holder 52 of a press machine 5, and the raw material 1 of magnesium base alloy inserted in an upper tubular space 52a of the upper pattern 2 of the holder 52 is pressed by a punch 51 of the press machine 5, so that the small-diameter magnesium base alloy tube can be extruded and formed.

In this case, the penetration holes 32 of the lower pattern 3 have the upper part in which the protrusions are inserted formed in drawing parts 32a in which a specified tube forming space is formed, and the lower part is formed in leading-out parts 32b of the magnesium base alloy tube of larger diameter extruded and formed by the drawing part 32a.

The upper pattern 2 and the lower pattern 3 for composing the forming pattern are not designed to rotate relatively by inserting common pins in holes 23 of smaller diameter than those formed respectively in the upper pattern 2 and lower pattern 3.

As the raw material 1 of the magnesium base alloy, depending on the final product (application), various conventionally known magnesium base alloys may be used, but it is preferred to use any magnesium base alloys excellent in strength and mechanical properties, forging properties (extrusion forming performance), and others, such as AZ system (Mg—Al—Zn alloy) and WE system (Mg—Y-rare earth elements alloy).

Figure 5:
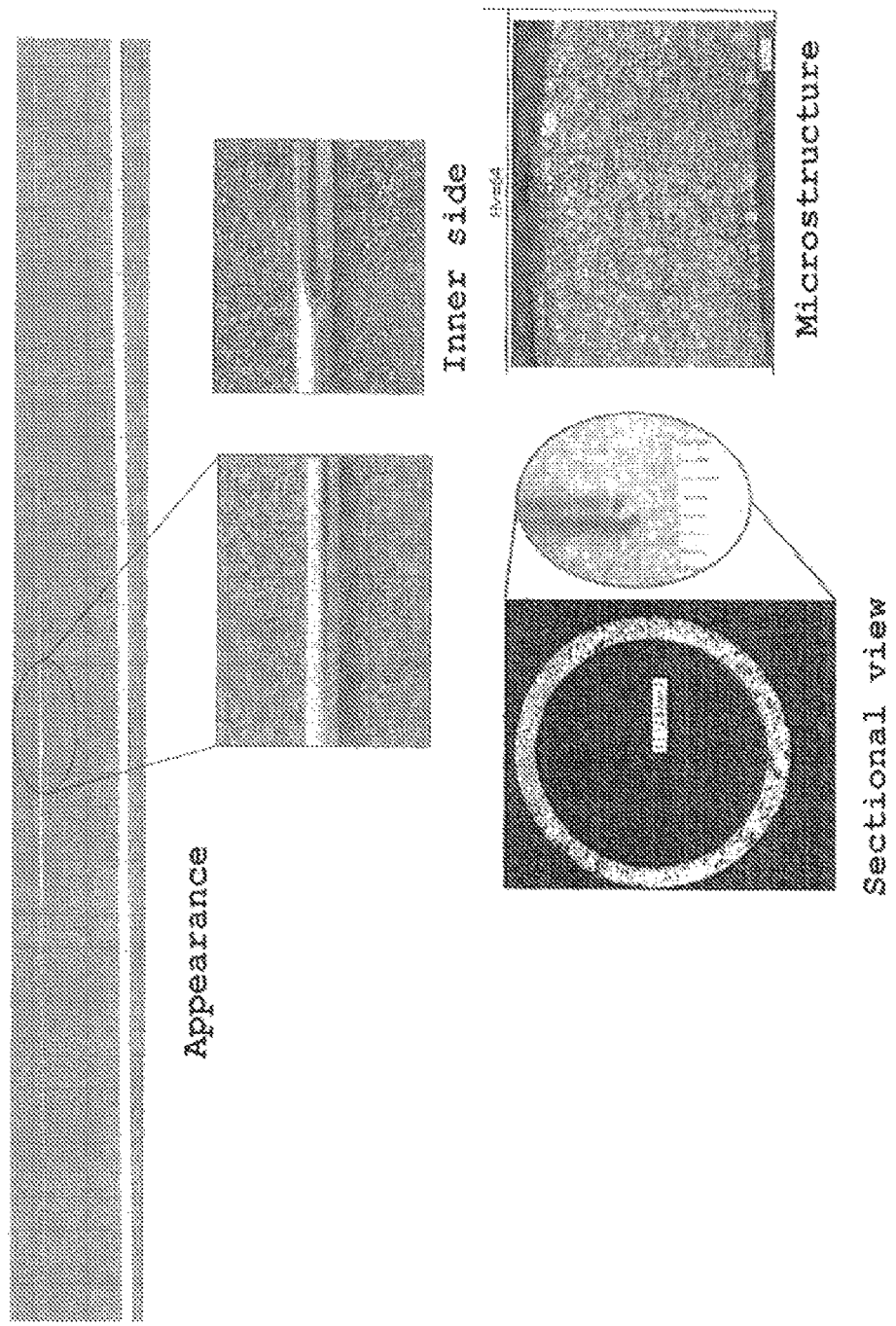
FIG. 5 is a photograph showing a magnesium base alloy tube.

Preferred examples of the raw material of the magnesium base alloy include powder and forging materials (such as columnar or cylindrical shapes suited to the tubular space 52a of the holder 52 of the press machine 5), and in relation to the use of the forming pattern consisting of the upper pattern and the lower pattern to be installed on the manufacturing apparatus, it is preferred to use a powder material capable of obtaining a uniform texture in the peripheral direction of the extruded and formed magnesium base alloy tube (such as those shown in the sectional view of the magnesium base alloy tube in FIG. 3 and FIG. 5).

Extrusion forming of the magnesium base alloy tube by this manufacturing apparatus may be either performed in cold process, but is more preferred to be done in a temperature condition of about 300° C. to 500° C., and more preferably the extrusion-formed magnesium base alloy tube may be treated, as required, thermally (heated and then cooled gradually).

The small-diameter magnesium base alloy tube manufactured by using this manufacturing apparatus is preferably 1.0 to 6.0 mm in outside diameter, 0.8 to 5.5 mm in inside diameter, 0.1 to 1.0 mm in wall thickness, and 500 mm or more in overall length, more preferably 1000 mm or more, and 20 μm or less in coaxiality, and 10% or more in elongation, and hence it is possible to obtain a small-diameter magnesium base alloy tube suited to manufacture of medical appliances such as stent, and long in length, high in dimensional precision, and excellent in mechanical properties.

Figure 4:
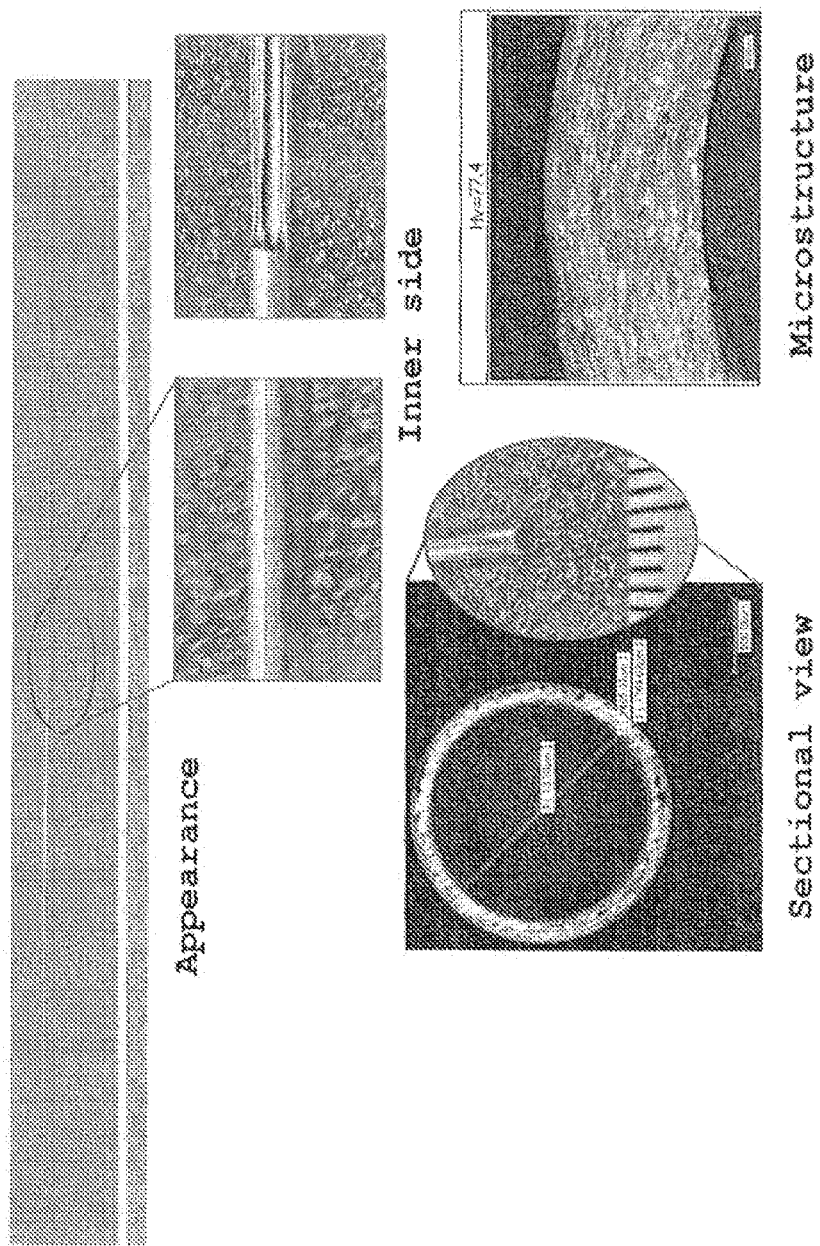
FIG. 4 is a photograph showing a magnesium base alloy tube.
Figure 6:
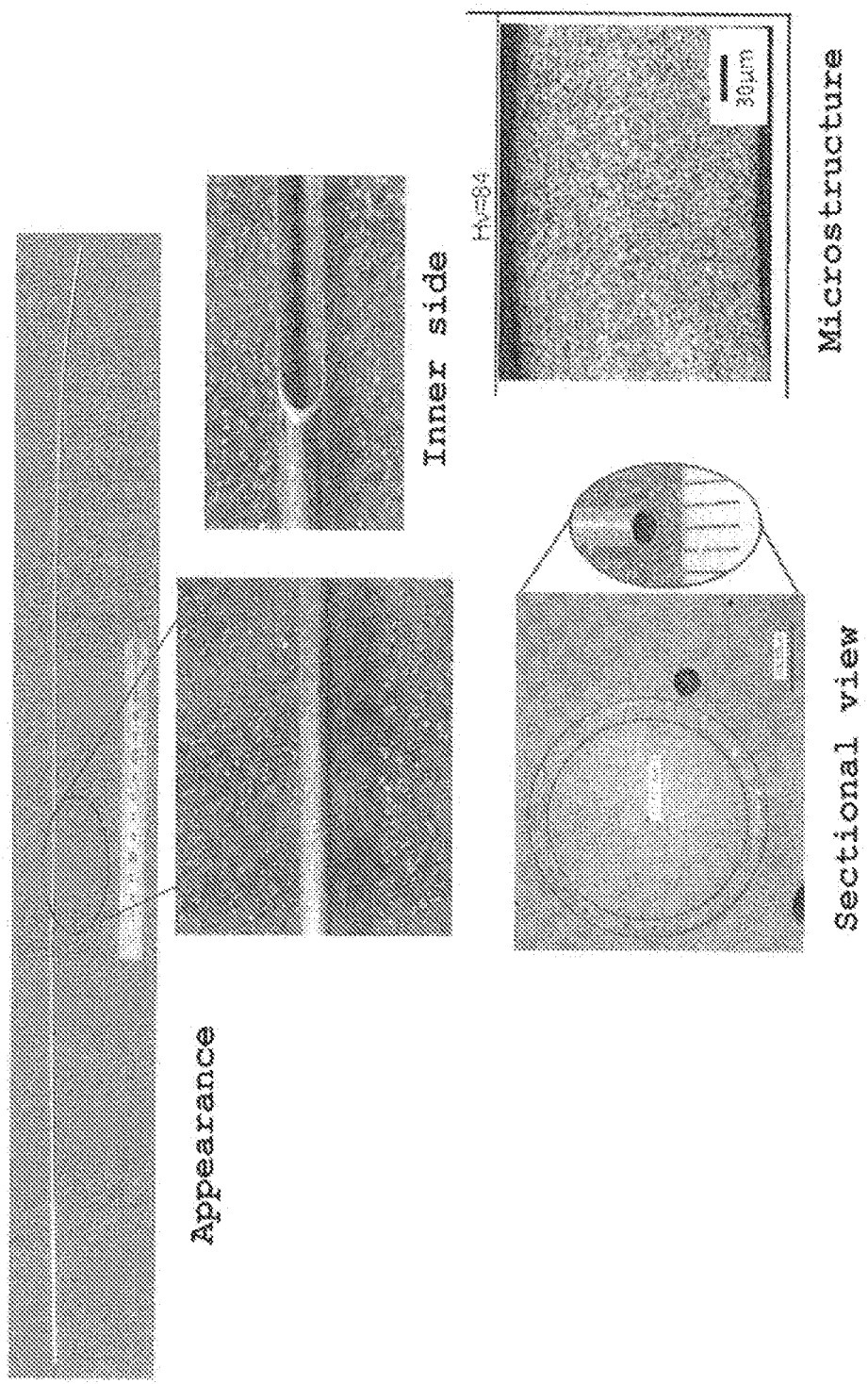
FIG. 6 is a photograph showing a magnesium base alloy tube.
Figure 7:
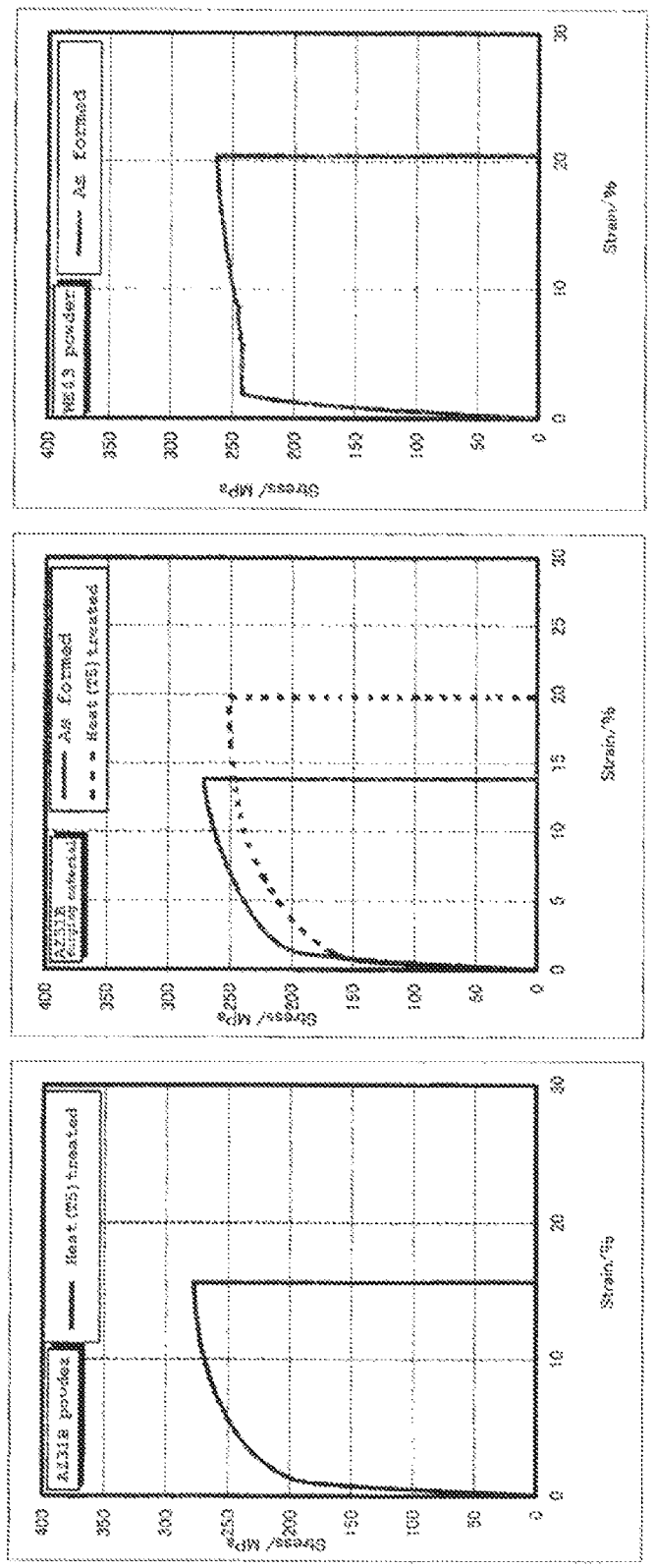
FIG. 7 is a graph showing a stress-strain curve of a magnesium base alloy tube.
Figure 8:
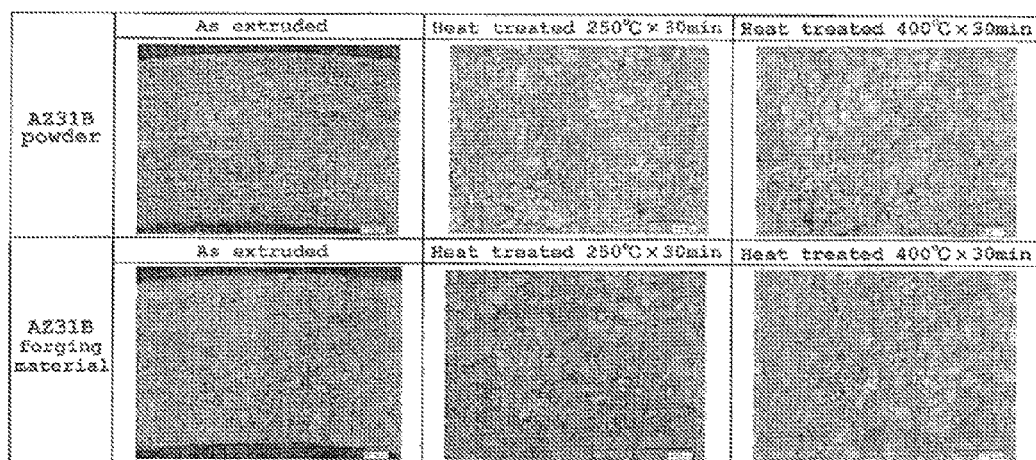
FIG. 8 is a graph showing a microscopic picture of a magnesium base alloy tube.

Specific examples of the small-diameter magnesium base alloy tube manufactured by using this manufacturing apparatus are shown in Table 1 and FIG. 4 to FIG. 6 (photograph), and their characteristic values (at the time of forming and heat (T5) treatment (heating then cooling gradually), including tensile strength: TS, yield strength: YP, yield ratio, yield ratio YP/TS, and elongation (EL) are shown in Table 2, the stress-strain curve in the tensile conditions (environmental temperature 25° C., strain speed 0.025 min−1) is shown in FIG. 7, and the microscopic pictures (at the time of forming and heating then cooing gradually) is shown in FIG. 8, respectively.

Herein, the overall length of the magnesium base alloy tube is 500 mm, but by adding and supplying the raw material 1, as required, a length of over 2000 mm can be also manufactured.

The coaxiality was measured by using a digital microscope VHX-2000 of Keyence, and measuring the center distance of an outside diameter circle (outer circumference) and an inside diameter circle (inner circumference) of an arbitrary section of the magnesium base alloy tube.

TABLE 1

| Raw material | Form | Outside diameter (mm) Inside diameter (mm) | Co-axiality (μm) | Roughness (outer circumference) Roughness (inner circumference) | Photo-graph |
|---|---|---|---|---|---|
| AZ31B | Powder | 1.795~1.805 1.487~1.491 | 13.7 | Ra0.10 Ra0.08 | FIG. 4 |
| AZ31B | Forging material | 1.799~1.806 1.386~1.401 | 12.8 | Ra0.10 Ra0.08 | FIG. 5 |
| WE43 | Powder | 1.793~1.819 1.379~1.408 | 11.3 | Ra0.08 Ra0.10 | FIG. 6 |

TABLE 2

STRENGTH PROPERTIES OF EXTRUDED SMALL-DIAETER TUBE

| | State | TS (MPa) | YP (MPa) | Yield ratio (YP/TS) | EL (%) | Remarks |
|---|---|---|---|---|---|---|
| AZ31B powder | As formed | 290 | 205 | 0.71 | 23.3 | Outside diameter φ2.0 |
| | Heat (T5) treated | 278 | 190 | 0.68 | 16.0 | Outside diameter φ1.8 |
| AZ31B forging material | As formed | 272 | 205 | 0.75 | 14.0 | Outside diameter φ1.8 |
| | Heat (T5) treated | 251 | 170 | 0.68 | 20.0 | Outside diameter φ1.8 |

TABLE 2-continued

STRENGTH PROPERTIES OF EXTRUDED SMALL-DIAETER TUBE

| | State | TS (MPa) | YP (MPa) | Yield ratio (YP/TS) | EL (%) | Remarks |
|---|---|---|---|---|---|---|
| WE43 powder | As formed | 263 | 220 | 0.84 | 20.0 | Outside diameter φ1.8 |

Heat (T5) treated: 400° C. × 60 min

Incidentally, the extrusion forming of small-diameter magnesium base alloy tube by this manufacturing apparatus is high in area reduction rate, and is hence high in the load applied to the forming patterns (upper pattern 2 and lower pattern 3), and therefore the forming pattern is likely to be deformed, buckled or broken.

To cope with this problem, as required, ultrasonic transmitters are disposed in the punch 51 and/or holder 21 (the forming pattern (upper pattern 2 and lower pattern 3) (not shown), and by adding ultrasonic oscillations at the time of forming, it is designed to reduce the abrasion resistance between the manufacturing apparatus such as forming patterns (upper pattern 2 and lower pattern 3), and the extruded and formed magnesium base alloy tube.

Figure 9:
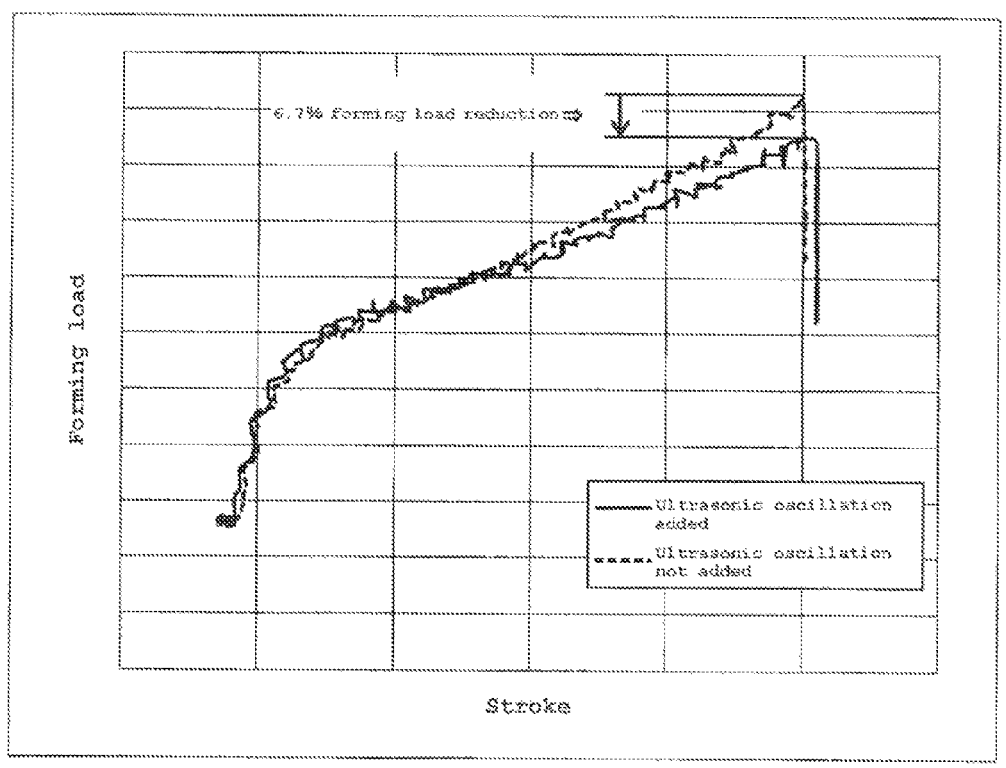
FIG. 9 is a graph showing fluctuations of foaming load in a case of adding and a case of not adding an ultrasonic oscillator at the time of forming.

As shown in FIG. 9, as clear from the variation graph of the forming load applied between a case of adding and a case of not adding an ultrasonic oscillator at the time of forming, by adding an ultrasonic oscillator at the time of forming, it has been confirmed that, as compared with a case of not adding, a forming load resistance effect of 6.7% can be obtained.

As a form of the raw material 1 of the magnesium base alloy, aside from the powder forging material mentioned above, it is also possible to use an extrusion forming material (a cylindrical shape suited to the tubular space 52a of the holder 52 of the press machine 5).

The extrusion forming material may be manufactured by using the extrusion forming machine 6 comprising an extrusion forming die 61 having an extrusion opening, and an extrusion tool 64 as shown in FIGS. 10A-10E.

The extrusion forming die 61 has a die unit 61a and a main body unit 61b.

In the magnesium base powder heating process, as shown in FIG. 10A, magnesium base powder 63 contained in the container 62 is heated to a specific temperature. A preferred heating temperature of the magnesium base powder is in a range of 0.6 Tm to 0.9 Tm, where Tm is the melting point of the magnesium base powder expressed in the absolute temperature.

In the magnesium base powder feeding process, as shown in FIG. 10B, the heated magnesium base powder 63 contained in the container 62 is supplied into the extrusion forming die 61 in its powder state. At the time of feeding the magnesium base powder 63 for the first time, a plug 67 for closing the extrusion opening of the disk unit 61a is disposed. This plug 67 is forced out from the extrusion die 61 together with the extrusion forming material 65 in which the magnesium base powder 63 is formed. Herein, the extrusion die 61 is heated, preferably at a temperature of 300° C. or more.

In the primary extrusion process, as shown in FIG. 10C, an extrusion tool 64 is pushed down, and the magnesium base alloy powder 63 in the extrusion die 61 is extruded. A preferred extrusion ratio of the extrusion process is 30 or more. At the end of the primary extrusion process, the extrusion forming material 65 is formed like a bar as being extruded outside from the extrusion outlet of the extrusion die 61, and a discarding part 65 is left over in the extrusion pattern 61 as the magnesium base power compressed body.

In the midst of primary extrusion forming process, preferably, in a different place, an additional magnesium base powder 63 in the container 62 is heated to a specific temperature.

In the additional magnesium base powder feeding process, as shown in FIG. 10D, the extrusion tool 64 is moved upward, and the additional magnesium base powder 63 in the container 62 is supplied into the extrusion die 61 in its powder state. The supplied additional magnesium base powder 63 is deposited on the discarding part 66 remaining in the extrusion die 61.

In the secondary extrusion process, as shown in FIG. 10E, the extrusion tool 64 is pushed down, and the discarding part 66 in the extrusion pattern 61 and the additional magnesium base powder 63 are extruded, for example, at an extrusion ratio of 30 or more. At the end of this secondary extrusion process, the discarding part 66 is left over in the extrusion pattern 61 as the magnesium base alloy powder compressed body. During the secondary extrusion process, preferably, the additional magnesium base powder 63 in the container 62 is heated to a specific temperature in a separate place.

By repeating this additional magnesium base powder feeding process, as shown in FIG. 10D, and secondary extrusion forming process, as shown in FIG. 10E, a very long extrusion material may be obtained.

In this manner, the extrusion forming material 65 thus obtained in this process may be cut in a length suited to the tubular space 52a of the holder 52 of the press machine 5, which may be used as a preferred raw material 1.

The small-diameter magnesium base alloy tube manufactured by using thus obtained extrusion forming material 65 in the raw material 1 of the magnesium base alloy undergoes two steps of extrusion forming process, and is processed into fine texture and high strength after the processing and curing process, and the mechanical properties are further excellent, and at the same time the corrosion resistance is further enhanced by corrosion core reduction and suppression of precipitation by solid solution of the magnesium base alloy.

The magnesium base alloy tube and its manufacturing method of the invention are specifically described while referring to exemplary embodiments, but the invention is not limited to the illustrated embodiments alone, but may be freely changed in the constitution and the application as far as it is not departed from the true spirit of the invention.

INDUSTRIAL APPLICABILITY

The magnesium base alloy tube and its manufacturing method of the invention are intended to present a small-diameter magnesium alloy tube long in length, high in dimensional precision, and excellent in mechanical properties, and can be hence applied preferably in manufacture of medical materials such as the stent, urinary tube, bile duct, and other internal tubular tissues by making use of the excellent biocompatibility of magnesium base alloy, and can be also applied in many structural materials in various industrial fields.

DESCRIPTION OF REFERENCE NUMERALS

1 Raw material
2 Upper pattern
21 Through-hole

22 Protrusion
3 Lower pattern
31 Concave part
32 Through-hole
4 Pin
5 Press machine
51 Punch
52 Holder
6 Extrusion apparatus

The invention claimed is:

1. A manufacturing method of a magnesium base alloy tube of which outside diameter is 1.0 to 6.0 mm, inside diameter is 0.8 to 5.5 mm, overall length is 500 mm or more, coaxiality is 20 µm or less, and elongation is 10% or more, the manufacturing method being a method of manufacturing a magnesium base alloy tube for extruding and forming a raw material of magnesium base alloy, by using a forming pattern comprising an upper pattern having circular cylindrical protrusions of a plate shape positioned in the center of plural through-holes so as to be surrounded by the plural through-holes for supplying the raw material into diaphragms of equal angles on the circumference, and a lower pattern having concave portions commonly penetrating at the exit of the plural through-holes of the upper pattern, and having through-holes for inserting the circular cylindrical protrusions of circular circumference of the upper pattern by providing a gap, positioned in the center of the concave portions in a circular columnar shape of the upper pattern.

2. The manufacturing method of the magnesium base alloy tube according to claim 1, wherein powder of magnesium base alloy is used as the raw material of the magnesium base alloy.

3. The manufacturing method of the magnesium base alloy tube according to claim 1, wherein forging material of magnesium base alloy is used as the raw material of the magnesium base alloy.

4. The manufacturing method of the magnesium base alloy tube according to claim 1, wherein extrusion forming material of magnesium base alloy is used as the raw material of the magnesium base alloy.

* * * * *